US009198967B2

(12) United States Patent
Cornelli

(10) Patent No.: US 9,198,967 B2
(45) Date of Patent: Dec. 1, 2015

(54) PHARMACEUTICAL COMPOSITIONS ACTIVE IN PREVENTING, STABILIZING AND TREATING ALZHEIMER'S DISEASE

(76) Inventor: Umberto Cornelli, Milan (IT)

(*) Notice: Subject to any disclaimer, the term of this patent is extended or adjusted under 35 U.S.C. 154(b) by 64 days.

(21) Appl. No.: 13/138,576

(22) PCT Filed: Mar. 5, 2010

(86) PCT No.: PCT/EP2010/052831
§ 371 (c)(1),
(2), (4) Date: Nov. 10, 2011

(87) PCT Pub. No.: WO2010/100257
PCT Pub. Date: Sep. 10, 2010

(65) Prior Publication Data
US 2012/0064054 A1    Mar. 15, 2012

(30) Foreign Application Priority Data

Mar. 6, 2009 (EP) .................................... 09425091

(51) Int. Cl.
*A61K 36/16* (2006.01)
*A61K 45/06* (2006.01)
*A61K 31/714* (2006.01)

(52) U.S. Cl.
CPC ............... *A61K 45/06* (2013.01); *A61K 31/714* (2013.01)

(58) Field of Classification Search
None
See application file for complete search history.

(56) References Cited

U.S. PATENT DOCUMENTS

| 6,733,797 B1 | 5/2004 | Summers |
| 2002/0182196 A1* | 12/2002 | McCleary .................. 424/94.1 |
| 2005/0249823 A1 | 11/2005 | Murphy et al. |
| 2006/0099239 A1 | 5/2006 | Coleman et al. |
| 2006/0257502 A1 | 11/2006 | Liu |

FOREIGN PATENT DOCUMENTS

WO    WO 02/100329    12/2002

OTHER PUBLICATIONS

Ono et al, Vitamin A exhibits potent antiamyloidogenic and fibril-destabilizing effects in vitro. Experimental Neurology (2004), 189(2), 380-392.*
Jia et al, High doses of nicotinamide prevent oxidative mitochondrial dysfunction in a cellular model and improve motor deficit in a *Drosophila* model of Parkinson's disease. Journal of neuroscience research, (Jul. 2008) vol. 86, No. 9, pp. 2083-2090.*
Davis, Comparative study of inhibition at multiple stages of amyloid-beta self-assembly provides mechanistic insight. Molecular pharmacology, (Aug. 2009) vol. 76, No. 2, pp. 405-413. Electronic Publication Date: May 29, 2009.*
Ryan et al, Correlating familial Alzheimers disease gene mutations with clinical phenotype. Biomarkers in Medicine, (Feb. 2010) vol. 4, No. 1, pp. 99-112.*
Corvol teaches Neuroprevention: A new challenge? Revue Neurologique, (Nov. 2012) vol. 168, No. 11, pp. 796-801.*
Bacskai, Four-dimensional multiphoton imaging of brain entry, amyloid binding, and clearance of an amyloid-beta ligand in transgenic mice. Proceedings of the National Academy of Sciences of the United States of America, (Oct. 14, 2003) vol. 100, No. 21, pp. 12462-12467.*
Aderinwale et al, Current therapies and new strategies for the management of Alzheimers disease. American Journal of Alzheimer's Disease and other Dementias, (Aug. 2010) vol. 25, No. 5, pp. 414-424.*
Schenk, Immunotherapy with beta-amyloid for Alzheimer's disease: a new frontier. DNA and cell biology, (Nov. 2001) vol. 20, No. 11, pp. 679-681.*
Zhang, Loss of function of ATXN1 increases amyloid beta-protein levels by potentiating beta-secretase processing of beta-amyloid precursor protein. The Journal of biological chemistry, (Mar. 19, 2010) vol. 285, No. 12, pp. 8515-8526.*
Nechiporuk, Linkage of familial Alzheimer disease to chromosome 14 in two large early-onset pedigrees: effects of marker allele frequencies on lod scores. American journal of medical genetics, (May 1, 1993) vol. 48, No. 1, pp. 63-66.*
McKhann G, Drachman Da, Folstein M et al Clinical diagnosis of Alzheimer's disease: Report of the NINCDS-ADRDA work group under the auspices of department of Health and Human Services task force on Alzheimer's disease. Neurology, 1984;34:939-944. (Spec, pp. 14 and 22).
Romàn GC, Tatemichi TK, Erkinjuntti T et al. Vascular dementia: diagnostic criteria for research studies: report of the NINDS-AIREN International Workshop. Neurology 1993;43:250-260. (Spec, pp. 14 and 22).
Cesarone MR, Belcaro G, Carratelli M, et al. A simple test to monitor oxidative stress, Int Angiol 1999;18:127-130. (Spec, p. 15).
Cornelli U, Terranova R, Luca S, et al. Bioavailability and antioxidant activity of some food supplements in men and women using the d-ROMs test as a marker of oxidative stress. J Nutr 2001 ; 131 :3208-3211. (Spec, pp. 15 and 23).
Seltzer B., Donepezil: an update. Expert Opin Pharmacother 2007:8:1011-1023. (Spec, p. 21).
Gray SL, Anderson ML, Crane PK et al. Antioxidant vitamin supplement use and risk of dementia or Alzheimer's disease in older adults. J Am Geriatr Soc 2008.56:291-295. (Spec, p. 21).
Malouf M, Grimley EJ, Areosa SA. Folic acid with or without vitamin B12 for cognition and dementia. Cochrane Database Syst Rev 2003;4:CD004514. (Spec, p. 21).
Aisen PS, Schneider LS, Sano M et al. High dose B vitamin supplementation and cognitive decline in Alzheimer disease: a randomized controlled trial. JAMA 2008,300:1774-1783 (Spec, p. 21).
Hawkins BT, Davis T. The blood-brain barrier/neurovascular unit in health and disease. Pharmacol Rev 2005;57:173-185. (Spec, pp. 2 and 26).

(Continued)

*Primary Examiner* — Qiuwen Mi
(74) *Attorney, Agent, or Firm* — Collard & Roe, P.C.

(57) ABSTRACT

The present invention relates to pharmaceutical compositions active in preventing, stabilizing and treating Alzheimer's disease and cognitive dysfunctions related thereto.

11 Claims, No Drawings

(56) References Cited

OTHER PUBLICATIONS

Wang J, Xiong S, Xie C et al. Increased oxidative damage in nuclear and mitochondrial DNA in Alzheimer's disease. J Neurochem 2005;93:953-962. (Spec, pp. 6 and 26).

Ding Q, Dimayuga E, Keller JN. Oxidative damage, protein synthesis, and protein degradation in Alzheimer's disease. Curr Alzh Res 2007;4:73-79. (Spec, pp. 6 and 26).

Lin MT, Beal MF. Mitochondrial dysfunction and oxidative stress in neurodegenerative diseases. Nature 2006;433:787-795. (Spec, pp. 5-6 and 26).

Lovell MA, Markesbery WR. Oxidative DNA damage in mild cognitive impairment and late-stage Alzheimer's disease. Nucleic Acids Res 2007;35:7497-7504. (Spec, pp. 6 and 26).

Zhu X, Smith MA, Honda K et al. Vascular oxidative stress in Alzheimers disease. J Neurol Sci 2007;257:240-246. (Spec, pp. 6-8 and 26-27).

Dröge W, Schipper MH. Oxidative stress and aberrant signaling in aging and cognitive decline. Aging Cell 2007;6:361-370. (Spec, pp. 6, 8 and 27).

Christen Y. Oxidative stress and Alzheimer disease. Am J Clin Nutr 2000;71 (suppl):621S-629S. (Spec, pp. 6, 8 and 27).

Hachinski V, Munoz DG. Cerebrovascular pathology in Alzheimer's Disease: cause, effect or epiphenomenon? Ann N Y Acad Sci 1997;826:1-6. (Spec, pp. 6 and 27).

Smith MA, Vasak K, Knipp M et al. Dimethylargininase, a nitric oxide regulatory protein, in Alzheimer's disease. Free Radc Biol Med 1998;25:898-902. (Spec, pp. 7 and 27).

Luth HJ, Holzer M, Gärtner U et al. Expression of endothelial and inducible NOS-isoforms is increased in Alzheimer's disease, in APP23 transgenic mice and after experimental brain lesions in rats: evidence for an induction by amyloid pathology. Brain Res 2001 ;913:57-67. (Spec, pp. 7 and 27).

Heneka MT, Wiesinger H, Dumitrescu-Ozimek L et al. Neuronal and glial coexpression of arginosuccinate synthetase and inducible nitric oxide synthase in Alzheimer disease. J Neuropathol Exp Neurol 2001 ;60:906-916. (Spec, pp. 7 and 27).

Soneja A, Drews M, Malinski T. Role of nitric oxide, nitroxidative and oxidative stress in wound healing. Pharmac Report 2005;57:108-119. (Spec, pp. 7 and 27).

Malinski T. Nitric oxide and nitroxidative stress in Alzheimer's Disease. J Alzheimers Dis 2007; 11 :207-218. (Spec, pp. 7 and 27).

Tagliavini F, Ghiso J, Timmers WF et al. Coexistence of Alzheimer's amyloid precursor protein and amyloid protein in cerebral vessel walls. Lab Invest 1990;62:761-767. (Spec, pp. 7 and 27).

Mohanty JG, Eckley DM, JD Williamson et al. Do red blood cell-β-amyloid interaction alter oxygen delivery in Alzheimer's disease? Adv Exp Med Biol 2008;614:29-35. (Spec, pp. 9, 16, 20, 24 and 27).

Singer SJ, Dewji NN. Evidence that Perutz's double-β-stranded subunit structure for β-amyloids also applies to their channel-forming structures in membranes. PNAS 2006; 103: 1546-1550. (Spec, pp. 9, 20 and 27-28).

Engström I, Ronquist G, Pettersson L, Waldenström A. Alzheimer amyloid beta-peptides exhibit ionophore-like properties in human erithrocytes. Eur J Clin Invest 1995;25:471-476. (Spec, p. 28).

Ravi LB, Mohanty JG Chrest FJ et al. Influence of beta-amyloid fibrils on the interactions between red blood cells and endothelial cells. Neurol Res 2004;26:579-585. (Spec, pp. 9 and 28).

Alhamdani MSS. Impairment of glutathione biosynthetic pathway in uremia and dialysis. Nephrol Dial Transplant. 2005;20: 124-128. (Spec, pp. 5, 9 and 28).

Reid M, Badaloo A, Forrester T, Jahoor F, in vivo rates of erythrocytes glutathione synthesis in adults with sickle cell disease. Am J Physiol Endocrinol Metab. 2006;291 :E73-E79. (Spec, pp. 9, 15, 23 and 28).

Andreyev AY, Kushnareva YE, Starkov AA. Mitochondrial Metabolism of Reactive Oxygen Species. Biochemistry (Moscow) 2005;70:200-214. (Spec, pp. 5 and 28).

Sas K, Robotka H, Toldi J, Vecsei L. Mitochondria, metabolic disturbances, oxidative stress and kynurenine system, with focus on neurodegenerative disorders. J Neurol Sci 2007;257:221-239. (Spec, pp. 5 and 28).

Marlatt M, Lee H, Perry G et al. Sources and mechanism of cytoplasmatic oxidative damage in Alzheimer's disease. Acta Neurobiol Exp. 2004;64:81-87. (Spec, pp. 6 and 28).

Hirai K, Aliev G, Nunomura A et al. Mitochondrial abnormalities in Alzheimers disease. J Neurosci 2001 ;21 :3017-3023. (Spec, pp. 6 and 28).

Mecocci P, Polidori MC, Cherubini A et al. Lymphocyte oxidative DNA damage and plasma antioxidants in Alzheimer disease. Arch Neurol 2002;59:794-798. (Spec, p. 28).

Stewart PA, Hayakawa K, Akers M-A, Vinters HV. A morphometric study of the blood-brain barrier in Alzheimer's disease Lab Invest 1992;67:734-742. (Spec, p. 28).

Blass JP, Gibson GE. The role of oxidative abnormalities in the pathophysiology of Alzheimer's disease. Rev Neurol (paris) 1991 ;147:513-525. (Spec, p. 28).

Metcalfe DD, Thompson HL, Klebanoff SJ, Henderson, Jr WR. Oxidative degradation of rat mast-cell heparin proteoglycan. Biochem J 1990;272:51-57. (Spec, pp. 6 and 28).

Roberts CR, Roughley PJ, Mort JS. Degradation of human proteoglycan aggregates induced by hydrogen peroxide. Biochem J 1989;259:805-811. (Spec, pp. 6 and 28).

Guiotto A, Calderan A, Ruzza P, Bonin G. Carnosine and carnosine-related antioxidants: a review. Curr Med Chem 2005;12:2293-2315. (Spec, pp. 4 and 28-29).

Hipkiss AR, Brownson C, Carrier MJ. Carnosine, the anti-ageing, anti-oxidant dipeptide, may react with protein carbonyl groups. Mech Ageing Dev 2001 ;122:1431-1445. (Spec, pp. 4 and 29).

Hipkiss AR. Could carnosine or related structures suppress Alzheimer's disease? J Alzheimers Dis 2007; 11 :229-240. (Spec, pp. 4 and 29).

Koltermann A, Hartkorn A, Koch E et al. Ginkgo biloba extract EGb® 761 increases endothelial nitric oxide production in vitro and in vivo. Cell Mol Life Sci 2007;64:1715-1722. (Spec, pp. 2, 5 and 29).

Napryeyenko O, Borzenko I, GINDEM-NP Study group. *Ginkgo biloba* special extract in dementia with neuropsychiatric features. A randomised placebo-controlled double-blind clinical trial. Arzneimittelforshung 2007;57:4-11. (Spec, pp. 2, 5 and 29).

Mazza M, Capuano A, Bria P, Mazza S. Ginkgo biloba and donepezil: a comparison in the treatment of Alzheimer's dementia in a randomized, placebo-controlled double-blind study. Eur J Neurol 2006;13:981-985. (Spec, pp. 2, 5 and 29).

Seshadri S, Beiser A, Selhub J et al. Plasma homocysteine as risk factor for dementia and Alzheimer's disease. NEJM 2002;346:476-483. (Spec, pp. 2 and 29).

Ravaglia G, Forti P, Maioli F et al. Homocysteine and folate as risk factors for dementia and Alzheimer disease. Am J Clin Nutr 2005;82:636-643. (Spec, pp. 2 and 29).

Babiloni, C, Bosco P, Ghidori R et al. Homocysteine and electroencephalographic rhythms in Alzheimer's disease. Neuroscience 2007;145, 942-954. (Spec, pp. 3 and 29).

Pogribna M, Melnik S, Pogribni I, Chango et al. Homocysteine metabolism in Children with Down Syndrome: In Vitro Modulation. Am J Human Genet 2001 ;69:88-95. (Spec, pp. 3 and 29).

Selkoe DJ. Normal and abnormal biology of the β-amyloid precursor protein. Annu Rev Neurosci 1994; 17:489-517. (Spec, pp. 3 and 29).

Näslund J, Haroutunian V, Mohs R et el. Correlation between elevated levels of amyloid β-peptide in the brain and cognitive decline. JAMA 2000;283:1571-1577. (Spec, pp. 3 and 29).

Kontush A. Amyloid-beta: an antioxidant that becomes a pro-oxidant and critically contributes to Alzheimer's disease. Free Rad Biol. Med 2001 ;31 :1120-1131. (Spec, pp. 4 and 29).

Butterfield DA. Amyloid beta-peptide (1-42)-induced oxidative stress and neurotoxicity: implications for neurodegeneration in Alzheimer's disease brain. A review. Free Rad Res 2002;36:1307-1313. (Spec, pp. 4 and 30).

Suo Z, Su G, Kundtz A et al. A beta vasoactivity in vivo. Ann N Y Acad Sci 2000;903:156-163. (Spec, pp. 4 and 30).

Cleary JP, Walsh DM, Hofmeister JJ et al. Natural oligomers of the amyloid-beta protein specifically disrupt cognitive function. Nat Neurosci 2005;8:79-84. (Spec, pp. 4 and 30).

(56) References Cited

OTHER PUBLICATIONS

Walsh DM, Selkoe DJ. Oligomers on the brain: the emerging role of soluble protein aggregates in neurodegeneration. Protein Pept Lett 2004; 11:213-228. (Spec, pp. 4 and 30).
Bleie Ø, Refsum H, Ueland PM et al. Changes in basal and postmethionine load concentration of total homocysteine and cystathionine after B vitamin intervention. Am J Clin Nutr 2004;80:641-648. (Spec, pp. 3, 16, 23-24 and 30).
Lee BJ, Huang MC, Chung LJ et al. Folic acid and vitamin B12 are more effective than vitamin B6 in lowering fasting plasma homocysteine concentration in patients with coronary artery disease. Eur J Clin Nutr 2004;58:481-487. (Spec, pp. 3 and 30).
McKinley MC, McNulty H, McPartlin J et al. Low-dose vitamin B6 effectively lowers fasting homocysteine in healthy elderly person who are folate and riboflavin replete. Am J Clin Nutr 2001; 73:759-764. (Spec, pp. 3 and 30).
Bønaa KH, Njølstad NJ, Ueland PM et al. Homocysteine lowering and cardiovascular events after acute myocardial infarction. NEJM 2006;354:1578-1588. (Spec, pp. 3 and 30).
Ebbing M, Bleie Ø, Ueland PM et al. Mortality Cardiovascular Events in Patients Treated With Homocysteine-Lowering B Vitamins After Coronary Angiography, JAMA 795-804 (2008). (Spec, p. 30).
Jatoi A, Kahanic SP, Frytak S et al. Donepezil and Vitamin E for preventing cognitive dysfunction in small cell lung cancer patients: preliminary results and suggestions for future study design. Support Care cancer. 2005;13:66-69. (Spec, pp. 22 and 30).
A. Venket Rao et al., "Role of Antioxidant Lycopene in Cancer and Heart Disease," Journal of the American College of Nutrition, vol. 19, No. 5, pp. 563-569 (2000).
Lee SC, Zhao ML, Hirano A, Dickson DW. Inducible nitric oxide synthase immunoreactivity in the Alzheimer disease hippocampus: association with Hirano bodies, neurofibrillary tangles, and senile plaques. J Neuropathol Exp Neurol 1999:58:1163-1169.
Mattiussi A.J., "*Niacin versus Niacinamide*", Can Med. Ass. J., 1992, 147 (7).
International Search Report of PCT/EP2010/052831, Jul. 8, 2010.
Written Opinion of the International Searching Authority of PCT/EP2010/052831, Jul. 8, 2010.

* cited by examiner

PHARMACEUTICAL COMPOSITIONS ACTIVE IN PREVENTING, STABILIZING AND TREATING ALZHEIMER'S DISEASE

CROSS REFERENCE TO RELATED APPLICATIONS

This application is the National Stage of PCT/EP2010/052831 filed on Mar. 5, 2010, which claims priority under 35 U.S.C. §119 of European Application No. 09425091.7 filed on Mar. 6, 2009, the disclosure of which is incorporated by reference. The international application under PCT article 21(2) was published in English.

FIELD OF THE INVENTION

The present invention relates to new pharmaceutical compositions containing antioxidants having direct or indirect activity at brain level, active in preventing, stabilizing and treating Alzheimer's disease.

STATE OF THE ART

In neurodegenerative diseases such as senile dementia of Alzheimer type (AD) as well as its prodrome forms thereof, such as mild cognitive impairment (MCI), an OS (oxidative stress) condition has long been observed, determinable by common indices of stress in plasma, as well as in cerebrospinal fluid (CSF) and post-mortem analyzed cerebral tissue.

Despite some uncertainty as to whether OS is an early cause or epiphenomenon, it remains clear that the elements involved are several and interconnected and that such elements can be altered either singly or as a whole.

For an accurate evaluation of cerebral OS, four key elements shall be considered: a) the blood-brain barrier; b) pro-oxidant components, such as amyloid and homocysteine; c) mitochondria; d) circulating cells with particular reference to erythrocytes.

a) The Blood-Brain Barrier (BBB)

The human brain is the most complex interrelated system in the body and, in terms of energy, requires $O_2$ and glucose in order to function.

Though comprising only about 2% of the body mass, the brain consumes almost 20% of the body $O_2$, being carried by about 14-16% of cardiac flow in an approximately 600 km network of cerebral vessels and microvessels.

Blood is supplied by passing across the blood-brain barrier (BBB), with metabolite removal primarily following the venous route and also, to a small extent, the CSF.

The brain has no lymphatic system and so drainage of proteins from the arterial-venous capillary interstitium, which in other parts of the body take place by this route, is dependent on the CSF and the venous system.

In contrast to other systems with high $O_2$ and energy consumption such as muscles which are monotonous in their activity (contraction/relaxation), the brain uses $O_2$ and energy in order to maintain and transfer information (mainly neuronal dendritic processes and astrocytes).

An endothelial lesion in the brain, in terms of physiological dynamics, erases the "information" contained within the brain cells served (dendritic processes, astrocytes) and can only be restored by "re-learning".

This latter process is highly complex, and may not even take place, nor be efficient, or can actually fail, such as in senile dementia.

Since cerebral neuronal structures cannot be replaced by duplication, all this indicates that with regard to maintaining cerebral function (plasticity) the entire system must operate at the highest level so as not to lose "information".

An important part of this complex system is the antioxidant network (AN).

The BBB is undoubtedly the structure most affected by the proper functioning of the AN as it is a very distinctive and well-organized interface compared to common endothelia present in the body.

The BBB is actually defined as a neurovascular unit [1] to highlight the importance of its interconnections. A lesion on any one of the elements within the neurovascular unit, be they neurons, astrocytes (including oligodendrocytes and gliocytes) or endothelial cells, leads to repercussions on its entire function.

The protection of the BBB, implemented by components of the AN, shall firstly take into account protection (direct and indirect) of vessels and their patency as well as those cells which are most associated with it, i.e. erythrocytes.

The indirect protection is carried out by components of the AN aimed at protecting membranes (i.e. vitamin E, vitamin C and Se), while direct protection is aimed at vessel patency using other components of the AN such as *Ginkgo biloba* flavonoids and terpenes, which also have considerable antioxidant power [35-37], but also at protection of erythrocytes.

b) Pro-Oxidant Components

Attention on this subject is focussed on two specific elements with oxidative capacity: homocysteine and amyloid substance.

Homocysteine is a long known cause of endothelial lesions [38, 39] to the extent that correlations have actually been proposed between levels thereof and EEG (electroencephalogram) changes in individuals with AD (Alzheimer's disease) [40]. Homocysteine is part of normal metabolism and is an important junction point as a methyl reserve, to be yielded for nucleic acid synthesis and cysteine formation which is then used for the synthesis of GSH (reduced glutathione) [41].

The significance of homocysteine levels is therefore evidently important, being dependent on a complex equilibrium whereby an inefficiency in any of the enzyme systems or a deficiency in any substrate such as the B-group vitamins (especially B6, B9, B12) causes an imbalance in its production. This has led to the supplemental use of these vitamins with the aim of reducing its levels in blood [49, 50], there being some differences of opinion regarding the need to use all of them or only B6 [51].

The efficiency of this metabolic junction point, however, also derives from reactivation of that part relative to GSH production, for which the availability of vitamins B1, B2 and B3 is also important. This reactivation enables a potentially oxidizing substance like homocysteine to be transformed into reducing equivalents such as GSH which can repair at least a part of the damage.

Therefore in seeking to face the homocysteine problem, the components to be used are all the B-group vitamins, except B5 which is not metabolically pertinent. However the latest clinical works [52] which have focussed on cardiovascular mortality have been disappointing with regard to the activity of B-group vitamins, to the extent that their use is not recommended.

The other lesion-forming substance, due to its oxidative capacity, is amyloid substance.

This forms from APP (amyloid precursor protein) through the action of two enzymes, α-secretase and γ-secretase [42, 43]. A third enzyme β-secretase, usually in equilibrium with α-secretase, can prevail over this latter and cleave from APP the Aβ 1-40 or Aβ 1-42 peptides which are amyloidogenic, deriving respectively from cerebral tissue (astrocyte neurons) or from vasal endothelium. These peptides aggregate to form amyloid substance.

The fundamental reasons whereby one enzyme system prevails over another are unknown, a more certain one being the overproduction of APP which is initiated when synaptic membrane repair is necessary, to hence sustain synaptic plasticity. If for any reason the synaptic repair mechanism is not regulated, repair will not be efficient and effective and the overabundance of amyloid peptides will trigger their aggregation to form amyloid substance, firstly in the form of diffuse plaques then with time in the form of senile plaques.

In brief, the presence of diffuse cerebral plaques and senile plaques (being older than diffuse ones) are evidence of a continuous attempt at repair resulting in aborted repair.

Aβ peptides have a bivalent action (antioxidant/pro-oxidant) but if produced in large amounts they are oxidants [44, 45] and have a constrictive effect on cerebral vessels [46].

Their presence generates local OS which affects proteins in the first instance. Since they are produced in the cells, firstly cellular OS increases then when the peptides are exported, they generate OS in the cell membrane environment with which they come into contact.

The reactive nature of these peptides gives them the ability to aggregate both naturally (in physiological solution), and, even more so, if brought into contact with substances able to trigger their polymerization, whether they be negatively or positively charged substances.

Those aggregated forms considered to be most toxic are soluble dimers and trimers [47, 48] which also create local OS, whereas the fibrillar form with more than 8-10 peptides has no neurotoxic activity.

Within the concept of physiological modulation, it is important to limit the oxidative burst by amyloidogenic peptides as it is self-sustaining; in other words, a Aβ peptide oxidizes a substrate which then enables it to aggregate.

The physiological modulation strategy is to limit this tendency by protecting the most easily oxidizable substrates, such as membrane proteins and phospholipids, with the AN.

Among the AN compounds, the physiological product that most complies with these characteristics is carnosine, as it protects proteins from amyloid-induced OS [32-34].

Amyloid, in its pre-fibrillar form, tends to bind to endothelium and its deposition, due to reactivity of the vessel, restricts microvessel size.

Therefore, it is sought to increase vessel size to enable improved vessel drainage, using typical AN compounds such as *Gingko biloba* flavonoids and terpenes [35-37], which have been demonstrated to possess this activity.

c) Mitochondria as Producers of Cerebral OS

As known, mitochondria are composed of four compartments, each one having specific functions: an outer membrane, relatively porous; an inner membrane, convoluted to form so-called crests; an intermembrane space charging with a H+ gradient; the mitochondrial matrix.

At least 7 known systems are known to generate ROS (reactive oxygen species) in the mitochondria, hence capable of producing OS, balanced by at least as many antioxidant systems [23]. Any change to the cytochromes of the respiratory chain has been observed to result in two parallel phenomena: reduced ATP (adenosine triphosphate) production and increased ROS production [4, 21, 24].

Also present in the matrix are NOSs (nitric-oxide synthetases) and consequently is NO. is generated. In case of respiratory chain dysfunction, an excess of $O_2.$ (superoxide) triggers production of $ONOO^-$ and subsequently of OH.

The contiguity of mtDNA (mitochondrial DNA), ribosomes and fatty acids present in the matrix allows their oxidation by the different ROSs arising from leakage in the energy production chain.

The abundance of endothelial mitochondria at the BBB is evidence for the energy required to maintain endothelial tight junctions, structures which can quickly change even in relation to systolic mechanical stress.

As now known, ATP production corresponds to production of $O_2.$ due to leakage and its transformation to $H_2O_2$ (hydrogen peroxide) through the superoxide dismutase (SOD). $H_2O_2$ has a reactive half-life enabling its diffusion, being able to spread into both the mitochondrial matrix and outside the mitochondrial membrane itself; in other words it exports oxidative stress (OS).

Mitochondrial DNA (mtDNA), being rich in guanosine bases, is among the first macromolecules to be attacked by this exporting.

Under cerebral OS conditions, commonly observed in senile dementia of the Alzheimer type (AD) or in MCI (Minimal Cognitive Impairment) which can precede it, there is an increased production of 8-OHdG (hydroxyl deoxyguanosine), a typical product of DNA oxidation. As a result, some of the cytochrome proteins which depend on mtDNA functioning will not be correctly synthesized by the ribosomal system, with consequent less of the energy needed for mitochondrial functions being produced [2-5].

MtDNA can even be repaired, though ATP is required to achieve this.

An initial compensation can derive from ATP imported from cytoplasmic glycolysis. Should this compensation enable the repair of damaged mtDNA, normality may be restored. If import of ATP cannot take place or is limited, the energy deficit will generate a vicious circle with further ROS production, leading to apoptosis and cell death.

Still within the context of OS in AD, an increase in oxidized proteins such as carbonylated proteins or AGE (glycosylated proteins) is noted, as well as oxidation of membrane lipids detected by an increase in isoprostanes, and finally the less well known oxidation of proteoglycans (PGs) [30, 31]. These latter, in view of their negative charges, initiate and stabilize amyloidogenic peptide aggregation and the formation of amyloid substance and neurofibrillary tangles (NFT).

All these oxidized derivatives have been found both in post-mortem brain tissue (particularly in those areas of the brain typically compromised in AD) and in biological fluids (blood, urine, CSF).

Analysis of mitochondrial functionality in AD subjects has highlighted defects in 3 systems related to energy metabolism: reduction in the activity of pyruvate dehydrogenase, α-keto-glutarate dehydrogenase and cytochrome oxidase [25, 26] Certainly, this condition implies that in individuals affected by AD, very premature vascular anomalies are observed, being characterized by loss of mitochondria in endothelial cells and thickening and splitting of basement membrane, with consequent loss of BBB function [6, 9].

The context in which AD and all its prodrome stages (such as MCI) develop has been undoubtedly connected to OS [7, 8].

The fact that OS is a cause or an epiphenomenon emerges as a false problem, in that OS in any event causes the disease to progress [3, 4].

If anything, the problem presented is how to face cerebral OS, by deciding which are the elements that keep it steadily high and which generate mitochondrial dysfunction or other conditions of oxidative stress.

As an initial element, a dysfunction in NO. production can be considered, with consequent repercussions on vascular tone.

As known, NO. synthesis depends on four synthetases, namely inducible (iNOS), endothelial (eNOS), neuronal (nNOS) as well as a fourth, defined as mitochondrial (mNOS) all of which use dimethylargininase to hydrolyze dimethy-larginine which enables NO. to be produced. Expression of dimethylargininase is dramatically increased in AD [10]. The consequence of all this is a general increase in NOS and in particular of iNOS both in glial cells and in hippocampus neurons [11-13].

Vasodilation would be expected which however does not arise since local conditions are also characterized by an increase in $O_2$. These events lead to formation of peroxynitrite ($ONOO^-$) followed by OH., and so instead of vasodilation the result is amplification of OS [14-15] with consequent vasoconstriction.

The concomitant presence of endothelial cell-derived amyloid peptide (Aβ), already in itself producing vasoconstriction [16], coupled with its deposition in the microvasculature, leads to narrowing of the lumen. The occurrence of abundant Aβ production is not random but related to the need for replacement, repair, plasticity and generally re-learning as previously defined. The final outcome of this whole process is reduced perfusion and an alteration in cerebral vessel functionality [6]. All this results in aborted repair, in other words NFT, amyloid substance, diffuse plaques and then senile plaques.

To provide protection of mitochondria with compounds of the AN it is necessary to: a) support coenzyme Q10 levels to protect the respiratory chain; b) support with vitamins B1, B2, B3 the pentose phosphate cycle which increases availability of cytoplasmic ATP for export in the mitochondria; c) increase availability of free GSH and that bound to antioxidant enzymes by supplying its precursors Se and L-cysteine.

d) The Final Significant Aspect of OS-Related Cerebral Modifications Concerns Circulating Cells, in the First Instance Erythrocytes Among all the circulating particles, erythrocytes are those most exposed to OS in that due to their very role as suppliers they are continuously in contact with those tissues from which they can absorb substantial damage.

As true frontier cells they can mirror tissue damage and can also undergo damage, in particular when contact with tissue is very close, as occurs in the brain, compelling them to an enforced deformability. If the vessel lumen, which very often consists of a single endothelial cell (as in the BBB), is then restricted due to pathological amyloid deposits, their physiology actually undergoes a morphologically demonstrable coarctation. [6-8].

The role of erythrocytes is to transport $O_2$ incorporated in haemoglobin and to protect the latter from oxidation. In view of the $O_2$ consumption by the cerebral system, the transportation capacity of erythrocytes and their ability to reach cerebral cells are fundamental elements for cerebral functionality.

Each erythrocyte contains 29 pg of haemoglobin corresponding to about 300 million haemoglobin molecules, which must be protected from oxidation to methemoglobin.

In methemoglobin, the heme $Fe^{2+}$ is oxidized to $Fe^{3+}$ (ferric ion) which is unable to hold $O_2$ binding instead to $H_2O$. In other words, by forming methemoglobin the erythrocyte loses $O_2$, or, rather, it loses transportation efficiency. In order to avoid all this, the erythrocyte is supplied with an antioxidant system, namely methemoglobin reductase, which is a NAD(P)H dependent enzyme. The erythrocyte must obtain these reducing equivalents (NAD(P)H) which it can obtain only by producing ATP from glycolysis by way of the pentose phosphate cycle. Its capacity for maintaining function hence depends on the functioning of this cycle.

The functional ability of erythrocytes depends not only on the protection of transported $O_2$, but also on the efficiency of the erythrocyte membrane which must have the necessary elasticity/deformability to better adapt itself to microvascular passage when the lumen is narrowed. All this means that the phospholipids and cholesterol in the membrane are not oxidized because this would cause it to harden.

Maintaining erythrocyte deformability requires it to provide for the oxidative repair of membrane structures, this being effected, as with haemoglobin, through the availability of reducing equivalents, again deriving from available APT from the pentose phosphate cycle.

In AD, erythrocytes are under stress. Aβ peptide binds to erythrocytes, not as such but in the dimeric or trimeric form, i.e. in the pre-fibrillar stage [17, 18]. Within this particular type of aggregation there forms a structure which produces pores in the erythrocyte membrane, altering its metabolism and changing its morphology, volume (increase) and deformability (rigidity).

Therefore export from the brain of Aβ (whether of vascular or tissue type, Aβ 1-40 and Aβ 1-42 respectively) in the pre-fibrillar form (hence premature) proceeds through the erythrocytes. They can deposit it onto the endothelium since their amyloid load increases their binding to the endothelium [20], particularly if, as a result of the reduced lumen, they are forced to marginate. In other words they can participate in forming a vicious circle if unable to take amyloid out of the BBB.

The erythrocytes have available the GSH synthetic pathway to implement the necessary regeneration of GSH, in particular when it has been used to detoxify liposoluble toxins [21, 22]. For GSH synthesis L-cysteine, glycine and glutamine are required (indeed GSH is a glutamyl-cysteinyl-glycine tripeptide) while to restore antioxidant enzymes such as glutathione peroxidase (GPx) Se is also needed, which when attached to cysteine, forms the peculiarity of selenocysteine; this particular amino acid allows enzyme activity over a wider pH range, as required for a more complete erythrocyte efficiency.

In view of the functions that these cells have to undertake, it is imperative that under conditions of cerebral oxidative stress they possess the necessary set of antioxidants.

In conclusion, analyzing the state of the art, as it results from the aforestated summary notes, it appears evident that in seeking to confront the problem of Alzheimer's disease or more generally the various stages of senile dementia it cannot be limited to assuming the administration of generic substances with antioxidant action to counteract cerebral OS, but individual causes of OS hitherto identified must be considered and an attempt made to identify other causes that have not yet emerged and which evidently have hitherto prevented arriving at a satisfactory solution to the problem.

SUMMARY OF THE INVENTION

We have now found a formulation of direct and indirect antioxidants, forming an aspect of the present invention, which acts on the four key elements liable to cerebral OS but which unexpectedly acts in a particular manner on erythrocytes, returning them at high percentages to their normal shape and motility and protecting these characteristics thereafter so as to ensure normal blood circulation in the brain and hence a correct functioning of all those mechanisms in the brain that depend on the necessary substances being introduced therein by red blood cells.

It is evident that elongation and hardening of red blood cells, i.e. their transformation into fusiform erythrocytes (FE), restricts or prevents their circulation though cerebral vessels and consequently prevents proper supply to the brain and consequent proper brain functioning. This in essence is what happens in the various stages of senile dementia, from minimum cognitive impairment (MCI) to Alzheimer's disease which represents the final stage and from which recovery is no longer possible. In individuals affected by Alzheimer's disease, fusiform erythrocytes (FE) are present on average in quantities greater than 15% of total erythrocytes.

The composition of the present invention contains direct and indirect oxidants (i.e. which do not have antioxidant activity in vitro) having the follows objects: a) to protect proteins, lipids, DNA, and proteoglycans (PGs) from oxidation, b) to reduce homocysteine levels, c) to sustain the pentose-phosphate cycle in circulating cells. Among known compounds able to act on the brain in the desired manner, the following have been identified and selected: carnosine, thiamine (vitamin B1), riboflavin (vitamin B2), nicotinamide (amide of vitamin B3), pyridoxine (vitamin B6), folic acid (vitamin B9), cyanocobalamin (vitamin B12), vitamin C, vitamin E, coenzyme Q10, β-carotene, selenium, L-cysteine and Ginkgo biloba extract.

More precisely, the single components have the following specific activity: carnosine protects brain proteins from the oxidizing action of amyloid which produces AGEs (Advanced Glycosylation End-products) and cross-linking; vitamins B1, B2 and B3 sustain the pentose phosphate cycle in erythrocytes and in brain cells; vitamins B6, B9, B12 reduce plasma levels of HCy; Se and L-cysteine increase GSH production; coenzyme Q10 improves mitochondrial function; vitamin E, beta-carotene and vitamin C protect membranes from oxidation; *Ginkgo biloba* produces vasodilation in the micro/macro-circulation and provides general antioxidant support to the system. All said specific activities give a surprising and unexpected synergic effect to the resulting pharmaceutical composition of the invention.

Furthermore, the optimal dosages and mutual proportions to act against cerebral oxidative stress were then identified for the each component of said composition, the dosages being in any event lower than the RDA.

DETAILED DESCRIPTION OF THE INVENTION

Surprisingly, the composition of the invention has been shown to protect erythrocytes from oxidative stress (OS) which is generated in patients affected by Alzheimer's disease, leading to the deformation of said erythrocytes transforming them into fusiform erythrocytes (FE) which lose their functional ability to deliver $O_2$ to the brain and to remove amyloid substance away from the brain. The term "to protect from OS" means that fusiform erythrocytes (FE) are returned to their normal structure and are protected during the execution of their function, and so remove amyloid substances and release them outside the brain in tissues able to metabolize them (e.g. liver, spleen).

The effect of the composition of the invention on FE is measured by the percentage difference in fusiform erythrocytes present in the patient's blood before and after treatment with the composition of the invention.

Thus the present invention concerns a pharmaceutical composition comprising carnosine, thiamine, riboflavin, nicotinamide, pyridoxine, folic acid, cyanocobalamin, vitamin C, vitamin E, coenzyme $Q_{10}$, β-carotene, selenium, L-cysteine, and *Ginkgo biloba* extract.

Preferably, said pharmaceutical composition comprises 40 to 50 wt % of carnosine, 0.5 to 1 wt % of thiamine, 0.5 to 1 wt % of riboflavin, 5 to 12 wt % of nicotinamide, 0.6 to 1.4 wt % of pyridoxine, 10 to 20 wt % of vitamin C, 5 to 12 wt % of vitamin E, 1 to 7 wt % of coenzyme $Q_{10}$, 0.5 to 5 wt % of β-carotene, 1 to 7 wt % of L-cysteine, 8 to 15 wt % of *Ginkgo biloba* extract.

More preferably, said pharmaceutical composition comprises 42 to 45 wt % of carnosine, 0.6 to 0.8 wt % of thiamine, 0.6 to 0.8 wt % of riboflavin, 6 to 10 wt % of nicotinamide, 0.8 to 1.2 wt % of pyridoxine, 12 to 15 wt % of vitamin C, 7 to 10 wt % of vitamin E, 3 to 6 wt % of coenzyme $Q_{10}$, 1.5 to 3 wt % of β-carotene, 3 to 6 wt % of L-cysteine, 10 to 13 wt % of *Ginkgo biloba* extract.

In a preferred embodiment, the pharmaceutical composition consists of 44.5 to 45 wt % of carnosine, 0.6 to 0.7 wt % of thiamine, 0.65 to 0.75 wt % of riboflavin, 7.5 to 9 wt % of nicotinamide, 0.8 to 1 wt % of pyridoxine, 0.07 to 0.1 wt % of folic acid, 0.0004 to 0.0007 wt % of cyanocobalamin, 13 to 14 wt % of vitamin C, 8.5 to 9.5 wt % of vitamin E, 4 to 5 wt % of coenzyme $Q_{10}$, 2 to 2.5 wt % of β-carotene, 0.01 to 0.02 wt % of selenium, 4 to 5 wt % of L-cysteine, and 11 to 12 wt % of *Ginkgo biloba* extract.

In a further aspect, the present invention concerns the use of said pharmaceutical composition for the preparation of a medicament for preventing, stabilizing and treating Alzheimer's disease and cognitive dysfunctions connected thereto.

Advantageously, for that use the single components are present in the composition in an amount equal to or less than the RDA (Recommended Daily Allowance).

Preferably, a unitary dose of said pharmaceutical composition comprises 90 to 110 mg of carnosine, 1.2 to 1.7 mg of thiamine, 1.4 to 1.8 mg of riboflavin, 14 to 24 mg of nicotinamide, 1 to 3 mg of pyridoxine, 25 to 42 mg of vitamin C, 12 to 25 mg of vitamin E, 5 to 15 mg of coenzyme $Q_{10}$, 2 to 9 mg of β-carotene, 5 to 15 mg of L-cysteine, 20 to 32 mg of *Ginkgo biloba* extract.

According to a preferred embodiment, a unitary dose of said pharmaceutical composition consists of carnosine 100 mg, thiamine (vitamin $B_1$) 1.4 mg, riboflavin (vitamin $B_2$) 1.6 mg, nicotinamide (amide of vitamin $B_3$) 18 mg, pyridoxine (vitamin $B_6$) 2 mg, folic acid (vitamin $B_9$) 200 μg, cyanocobalamin (vitamin $B_{12}$) 1 μg, vitamin C 30 mg, vitamin E 20 mg, coenzyme Q10 10 mg, β-carotene 800 RE, selenium 27.5 μg, L-cysteine 10 mg and Ginkgo biloba extract 25 mg, as also shown in Table 1.

Table 1 refers to the composition of said preferred embodiment as Formula F, further reporting the RDA values concerned except for vitamin E which was used at 200% RDA (as the racemic form was used). As can be seen the reported dosages were found to be useful for preparing the composition and for obtaining the required results at the various stages of senile dementia and in particular Alzheimer's disease, are very low, being between 25% and 100% of the RDA.

TABLE 1

| Formula F | | |
|---|---|---|
| | Dose | RDA |
| Carnosine | 100 mg | — |
| Thiamine (vitamin $B_1$) | 1.4 mg | 100 |
| Riboflavin (vitamin $B_2$) | 1.6 mg | 100 |
| Nicotinamide (amide of vitamin $B_3$) | 18 mg | 100 |
| Pyridoxine (vitamin $B_6$) | 2 mg | 100 |

TABLE 1-continued

Formula F

| | Dose | RDA |
|---|---|---|
| Folic acid (vitamin $B_9$) | 200 µg | 100 |
| Cyanocobalamin (vitamin $B_{12}$) | 1 µg | 100 |
| Vitamin C | 30 mg | 50 |
| Vitamin E | 20 mg | 200 |
| Coenzyme $Q_{10}$ | 10 mg | — |
| β-carotene | 800 RE* | 100 |
| Selenium | 27.5 µg | 25 |
| L-cysteine | 10 mg | — |
| *Ginkgo biloba* extract | 25 mg | — |

*RE means retinol equivalents, where 1 RE = 6 µg β-carotene

The composition given in Table 1 refers to a preferred unitary dose, but the same can be daily administered in an amount of 30 to 300% depending on the seriousness of the disease to treat, i.e. depending on the stage of cerebral distress for which intervention is required.

In any case, one of the fundamental aspects found is that improving erythrocyte OS is not possible by using only antioxidants particularly suited to act thereon, but antioxidants that act on other specifically identified components of the cerebral system shall also be used.

Only with this comprehensive and synergic action, it was resulted to be possible to achieve an unexpectedly significant reduction in FE and consequently a significant improvement of the pathology, this being probably related to the greater removal of amyloid substance from the cerebral mass and, in any case, to an improved blood circulation in the brain with consequent reactivation of all cerebral mechanisms.

In order to make more evident the surprising results and advantages achieved by the pharmaceutical composition of the invention, all the data are herein below reported showing the effects of a clinical study undertaken with a significant number of patients.

In order to determine reduction in FE and whether a reduction in FE has the clinical effect of reducing disease progression (i.e. severity of Alzheimer's disease (AD)), the composition was administered together with donepezil for 6 months to patients affected by AD and compared to a group treated with donepezil and a placebo. Administration of donepezil was necessary in that individuals affected by AD cannot be treated with placebo alone.

Donepezil is a known cholinesterase inhibitor and already used in AD and cognitive disorders in general.

Clinical Study

A cohort of 52 patients affected by AD was randomly divided into two groups which were monitored for a period of 6 months according to a double-blind design. One group of 26 subjects was treated with Formula F in a 2-phase ampoule (powder in the lid and diluent in the ampoule to be reconstituted at the time of consumption); another group of 26 subjects was treated with a placebo indistinguishable from Formula F. The trial was conducted in patients already undergoing therapy with donepezil.

The patients suffered from AD according to the NINCDS-ADRDA and NINDS-AIREN criteria [McKhann G, Drackman Da, Folstein M et al Clinical diagnosis of Alzheimer's disease:-report of the NINCDS-ADRDA work group under auspices of department of Health and Human Services task force on Alzheimer's disease. Neurology, 1984; 34:939-944.

Romàn G C, Tatemichi T K, ErkinjunttiT et al. Vascular dementia: diagnostic criteria for research studies: report of the NINDS-AIREN International Workshop. Neurology 1993; 43:250-260]. Subjects accepted were those with MMSE II >21 with a diagnosis of probable AD, already on donepezil treatment for at least 2 months at a dose of 5 mg/day and on stable treatment for at least 3 months in case of other concomitant chronic diseases. The allele ApoE ε type was not considered as an inclusion or exclusion criterion but only as a descriptive variable. Patients who were not assisted by caregivers were excluded, as were patients with malignant tumours or those undergoing chemotherapy. Also excluded were patients with a MMSE II score <21, with alcohol abuse, or affected by depression, or those on donepezil therapy for less than 2 months, or on a dosage of >5 mg/day.

The majority of exclusions were due to disease severity (MMSE II <21) or to only a brief treatment period with donepezil (<2 months) or the fact that the subjects were being treated with drugs other than donepezil.

All the patients took donepezil at a dose of 5 mg/day. One group was treated with Formula F at a dose of 1 ampoule/day in the morning, immediately before breakfast; another group was treated with placebo (excipients plus 500 mg of fructose and flavourings). Placebo and Formula F were identical in appearance.

All the treatments were administered for a period of 6 months.

The main parameter was OS measurement using the d-ROMs test on plasma [Cesarone M R, Belcaro G, Carratelli M, et al. A simple test to monitor oxidative stress. Int Angiol 1999; 18:127-130.

Cornelli U, Terranova R, Luca S, et al. Bioavailability and antioxidant activity of some food supplements in men and women using the d-ROMs test as a marker of oxidative stress. J Nutr 2001; 131:3208-3211].

HCy, GSH and the number of FEs were regarded as secondary parameters. Evaluation of MMSE II was also regarded as a secondary parameter.

Laboratory Values and Rating Scales

During the assessments blood was collected, after fasting since the previous evening, into heparinized and non-heparinized tubes. Aliquots of 5 ml were collected (2 of plasma and 1 of serum) from the brachial vein. The collected blood was immediately centrifuged and kept at −80° C. until required for the measurements. A fourth aliquot of 2 ml, without heparin, was collected for FE analysis.

The d-ROMs test [Cornelli U, Terranova R, Luca S, et al. Bioavailability and antioxidant activity of some food supplements in men and women using the d-ROMs test as a marker of oxidative stress. J Nutr 2001; 131:3208-3211], erythrocyte GSH [Reid M, Badaloo A, Forrester T, Jahoor F. In vivo rates of erythrocyte glutathione synthesis in adults with sickle cell disease. Am J Physiol Endocrinol Metab. 2006; 291:E73-E79] and HCy [Bleie Ø, Refsum H, Ueland P M et al. Changes in basal and post-methionine load concentration of total homocysteine and cystathionine after B vitamin intervention. Am J Clin Nutr 2004; 80:641-648.] were evaluated by standardized methods. The d-ROMs test was evaluated at each assessment while the other tests were evaluated only at the basal and the 6-month assessments.

FE measurements were carried out by isolating the erythrocyte pellet by centrifugation (100×g for 15 minutes at 4° C.) and diluting it in 2 ml of a citrate-phosphate-dextrose solution with adenine (CPDA) then centrifuged once more.

After centrifugation the upper part of the solution was removed and the process repeated three times always resuspending with CPDA.

Immediately after the last preparation, FE percentage was calculated using a microscope with Nomarski optics based on an analysis of 400 erythrocytes [Mohanty J G, Eckley D M, J D Williamson et al. Do red blood cell-β-amyloid interaction alter oxygen delivery in Alzheimer's disease? Adv Exp Med Biol 2008; 614:29-35.]

Evaluation of MMSE II was carried out during the basal period and after 3 and 6 months, not more than one day after blood withdrawal. A variation of at least 1 MMSE II point relative to the basal value was regarded as being clinically significant as an improvement or a deterioration. Sleep quality was measured according to a semi-quantitative scale (no change, improvement, deterioration).

The sample size was determined on the basis of the d-ROMs test, which is a measure of OS. Preliminary open-label tests on patients affected by AD two months following the antioxidant treatment addressed the extent of possible variations. In these tests a reduction was observed of at least 70-80±10 (Standard Deviation or SD) U. CARR corresponding to a 20% reduction/increase on the basal values. In the untreated group fluctuations of 20±10 U. CARR. were observed which corresponded to a no more than a 5% reduction/increase on the basal values.

Considering that $\alpha=0.05$ and $1-\beta=0.9$, groups of 20 subjects are sufficient for obtaining a discriminatory power of >0.9. Also, allowing for a maximum drop-out of 30%, it was decided to enroll 26 subjects per group. For each variable the means±SD were calculated.

The differences between groups were determined on the basis of the t-test for independent and interdependent data. Moreover, the correlation coefficients were calculated between the variables under examination. To determine the differences between the improvement/deterioration frequencies observed in the two groups the exact chi-square test according to Fisher was employed.

Results

Only 48 of the initial 52 patients completed the trial; 23 cases treated with Formula F and 25 cases treated with placebo. The general characteristics of the patients are given in table 2.

TABLE 2

Characteristics of the patients treated with Formula F or with Placebo

| Variables | Formula F | Placebo | p |
|---|---|---|---|
| Sex | 9 males; 14 females | 10 males; 15 females | ns |
| Age | 75 ± 4.2 | 74 ± 4.9 | ns |
| Hypertension | 6 | 5 | ns |
| NIDD | 6 | 5 | ns |
| PMI | 5 | 6 | ns |
| Dyslipidemia | 6 | 6 | ns |
| ApoE ε 4[a] | 4 | 5 | ns |

NIDD = non-insulin dependent diabetes; PMI = prior myocardial infarction (at least 3 years before). Some patients were also affected by other pathologies (urological/gynecological) but their frequency was too low to be discriminatory. P = chi-square test with Yates correction or t-test for independent data; ns = p > 0.05.
[a]At least one ε 4 allele.

Antioxidant treatment was very well tolerated and no noteworthy side effects were observed. Compliance was excellent in both groups.

There was no salient change in any of the concomitant illnesses (hypertension, type II diabetes, dyslipidemia) as a result of the treatments, neither were major variations in sleep quality observed.

Table 3 gives values for the laboratory analyses: basal data and data after 6 months of treatment.

TABLE 3

Laboratory values in patients affected by AD

| Variable | Period | Formula F | Placebo |
|---|---|---|---|
| d-ROMs test [U.CARR.] | Basal | 380 ± 44.6 | 365 ± 37.8 |
|  | 6 months | 295 ± 26.3[ab] | 356 ± 40.2 |
| HCy μmol/L | Basal | 27 ± 5.4 | 29 ± 5.9 |
|  | 6 months | 20 ± 2.9[ab] | 27 ± 2.3 |
| GSH μmol/mL | Basal | 2.6 ± 0.72 | 2.9 ± 0.84 |
|  | 6 months | 3.2 ± 0.82[a] | 3.0 ± 0.79 |
| FE[c] % | Basal | 18 ± 4.4 | 20 ± 4.2 |
|  | 6 months | 12 ± 3.8[ab] | 17 ± 3.7[a] |

Values are given as mean ± DS;
[a]t-test p < 0.05 for interdependent data (basal vs 6 months);
[b]t-test p < 0.05 for independent data (Formula F vs placebo at 6 months);
[c]For the group treated with Formula F the measurement related to 20 subjects only.

Reduction in OS was observed only in patients treated with Formula F. The number of FE was reduced even in the placebo-treated group, probably as an effect of donepezil, but the effect on this variable is significantly greater (p<0.05) following treatment with Formula F.

Measurements relative to MMSE II at basal then after 3 and 6 months are collected in table 4.

TABLE 4

MMSE II in the two patient groups: mean values ± SD

| Treatment | Period | MMSE II | Improved/deteriorated cases |
|---|---|---|---|
| donepezil + Formula F | Basal | 23.2 ± 1.14 |  |
|  | 3 months | 24.0 ± 1.57 | 4/0 |
|  | 6 months | 24.3 ± 1.43 | 11[a]/1 |
| donepezil + placebo | Basal | 23.9 ± 1.04 |  |
|  | 3 months | 23.6 ± 1.11 | 0 |
|  | 6 months | 24.2 ± 1.28 | 4/2 |

[a]Exact chi-square (Fisher) p < 0.05 (Formula F vs placebo)

An improvement in average MMSE II was observed in both groups.

However, with the individual cases, an improvement in MMSE II (≥+1) was observed in 12 cases treated with Formula F and in only 4 cases treated with placebo. This difference is significant according to the Fisher test (p<0.05).

A single reduction in MMSE II (≤−1) was recorded in the antioxidant-treated group and in two of the cases treated with placebo.

The correlation coefficients between the different variables were calculated for the group treated with Formula F (Table 5) based on the differences between the 6 month values and basal values.

The same calculation was not possible for the group treated with placebo due to the limited number of improvements.

TABLE 5

Correlation coefficients for all the variables of the group treated with Formula F

| Variable | MMSE II | d-ROMS test | HCy | EF | GSH |
|---|---|---|---|---|---|
| MMSE II | 1 |  |  |  |  |
| d-ROMS test | 0.388 | 1 |  |  |  |
| HCy | 0.242 | −0.194 | 1 |  |  |
| FE[a] | 0.816[b] | 0.489[c] | 0.179 | 1 |  |
| GSH | 0.881[b] | 0.499[c] | 0.307 | 0.621[b] | 1 |

[a]The value relates to 20 cases only;
[b]p < 0.01;
[c]p < 0.05

Some significant correlations were observed between the differences in MMSE II values (value at 6 months-basal value) and reduction of FEs. The increase in GSH was also correlated with the MMSE II improvement. The d-ROMs test reduction was correlated both with the FE reduction and the increased GSH.

The reduction in FE and the increase in GSH were shown to be highly correlated (p<0.01).

All the variables were evaluated to determine possible basal data correlations by combining the values of the two groups, but no correlation was found to be significant. This indicates that it was the treatment with Formula F to have resulted in the significant differences, because with donepezil alone there were no such correlations.

On the basis of these results the following conclusions can be drawn.

Treatment with Formula F has been shown to reduce OS and to improve the clinical effects of donepezil.

The data which demonstrate FE reduction are surprisingly significant. As previously mentioned erythrocytic deformation resulting in FE can be correlated with the presence of amyloid substance [Mohanty J G, Eckley D M, J D Williamson et al. Do red blood cell-β-amyloid interaction alter oxygen delivery in Alzheimer's disease? Adv Exp Med Biol 2008; 614:29-35.

Singer S J, Dewji N N. Evidence that Perutz's double-β-stranded subunit structure for β-amyloid also applies to their channel-forming structures in membranes. PNAS 2006; 103: 1546-1550.] which alters $O_2$ delivery to the brain. After the treatment with Formula F, $O_2$ transport improved because erythrocytes tend to resume their normal shape and deformability to the extent of the increased antioxidant reserve (erythrocytic GSH) with a positive effect on microcirculation.

The improved erythrocyte functionality enables them to efficiently transport amyloid deriving from cerebral tissue and not to release it in the cerebral microcirculation.

This effect is important exactly for the high levels of amyloid substance depositing in the cerebral microcirculation which appear even before AD symptoms become evident.

On the whole, the increase in GSH levels was found to be proportional to the reduction in FE, both these variables having proved to be correlated with the MMSE II improvement.

However GSH measurement is exclusively a biochemical variable, whereas that of FE is purely functional. An increase in GSH could also arise without any change to the FE.

The combination of the two effects observed with the compositions of the present invention hence indicates a substantial improvement in both the antioxidant capacity and functionality i.e. the availability of $O_2$ to the brain, resulting in a favourable effect on cognitive and behavioural functions.

Donepezil as such has also produced an improvement in the FE probably in proportion to the reduced production of cerebral amyloid substance, a known effect of cholinesterase inhibitors [Setzer B. Donepezil an update. Expert Opin Pharmacother 2007: 8:1011-1023.] The addition of Composition F has significantly amplified said effect, confirming the relationship between erythrocyte functionality and clinical improvement.

When the correlations between the examined variables were carried out in the basal period (i.e. at the time when all the subjects were receiving only donepezil therapy) no correlation was found between the variables; that is to say MMSE II, HCy, dROMs, GSH, FE were not correlated either in the two groups, or in the groups as a whole.

At the end of the trial some correlations emerged relating only to the group treated with Composition F. This indicates that Formula F was responsible for the salient effects.

The reduction in HCy also appears to be important for the overall improvement of erythrocyte function, despite not having a direct impact on FE.

In conclusion it was established that the specific combination of antioxidants and the specific proportions used in Composition F achieves the effect of substantially improving the general situation of cerebral OS, by particularly and unexpectedly affecting FEs.

The results obtained indicate Composition F to be one way of preventing or slowing the effects of senile dementia in all subjects with risk factors for AD (in particular connected with age) even if symptoms are not yet clinically apparent. Limiting oxidative risk related to age has never been achieved with high dosage antioxidant administration: no effect on the onset and progression of AD has ever been verified [Gray S L, Anderson M L, Crane P K et al. Antioxidant vitamin supplement use and risk of dementia or Alzheimer's disease in older adults. J Am Geriatr Soc 2008. 56:291-295.

Malouf M, Grimley E J, Areosa S A. Folic acid with or without vitamin B12 for cognition and dementia. Cochrane Database Syst Rev 2003; 4:CD004514.] and on the contrary, negative effects have been noted on other chronic pathologies [Aisen P S, Schneider L S, Sano M et al. High-dose B vitamin supplementation and cognitive decline in Alzheimer disease: a randomized controlled trial. JAMA 2008, 300:1774-1783], Moreover, Composition F has been shown to clearly improve the cerebral clinical state in patients treated with donepezil, while combinations of this drug with other tested antioxidants in the past have not yielded positive results [Jatoi A, Kahanic S P, Frytak S et al. Donepezil and Vitamin E for preventing cognitive dysfunction in small cell lung cancer patients: preliminary results and suggestions for future study design. Support Care cancer. 2005; 13:66-69].

With the purpose of demonstrating if any one of the antioxidant group constituting the new composition of the invention was specifically and primarily responsible for the unexpected activity on the altered erythrocytes (FE), some experiments were conducted on elderly subjects affected by mild probable AD.

32 cases of mild (MMSE II >26) probable dementia (ADp) were analyzed according to the NINCDS-ADRDA criteria [McKhann G, Drackman Da, Folstein M et al Clinical diagnosis of Alzheimer's disease:—report of the NINCDS-ADRDA work group under auspices of department of Health and Human Services task force on Alzheimer's disease. Neurology, 1984; 34:939-944.

Roman G C, Tatemichi T K, ErkinjunttiT et al. Vascular dementia: diagnostic criteria for research studies: report of the NINDS-AIREN International Workshop. Neurology 1993; 43:250-260].

The inclusion criteria were: a) subjects of both sexes aged >60 years; b) on donepezil therapy for at least two months at a dose of 5 mg (for homogeneity of base treatment).

The exclusion criteria were: a) chronic pathologies other than ADp not therapeutically controlled; b) absence of caregivers who would ensure the ingestion of the products to be tested.

The subjects were randomly divided into four groups each composed of 8 subjects (4 males and 4 females) and they followed an experimental scheme of three test periods.

In the first period each group was subjected to one of four different treatments having an antioxidant effect, either direct or indirect, for a period of 2 weeks.

In the second test period all four groups were given a placebo treatment for a period of 15 days.

In the third test period all the subjects (32 in total) had to undergo a treatment represented by a combination of formulations A+B+C evaluated separately in the first experimental period (formulation D already formed part of formulation A).

In this manner the action of the single treatments could be compared with that of the combined treatments.

The placebo was inserted into identical ampoules to those of the antioxidants.

Treatments with Formula A, B, C or D were randomly assigned to the subjects. When the patients were subjected to assessment tests (basal and post-treatment) they were provided with a package containing 20 ampoules, identified only with the subject's number and treatment period (15-30-45).

The following antioxidant groups were evaluated (see Table 6).

a) a group of B vitamins able to reduce homocysteine levels and to activate the pentose phosphate cycle in circulating cells (particularly, but not only, in red blood cells (RBCs)).

b) a combination of carnosine, *Ginkgo biloba* and Coenzyme $Q_{10}$ able to protect cerebral proteins from oxidation produced by amyloid (carnosine) and to enable improved blood supply of the cerebral microvessels (*Ginkgo biloba*) and improved mitochondrial function (Coenzyme $Q_{10}$).

c) a combination of vitamin E, vitamin C, Se and L-cysteine which are the classic antioxidants acting in a coordinated manner for vitamin E regeneration and for GSH synthesis.

d) a combination of solely vitamins $B_6$, $B_9$ and $B_{12}$.

The experimental scheme enabled evaluation of whether, and for which analyzed variable, the effect of the combination was greater than the effect of the single formulations to be evaluated.

Oxidative stress was determined with d-ROMs [Cornelli U., Terranova R., Luca S. et al. Bioavailability of some food supplementation in man and women using d-ROMs test as a marker for oxidative stress. J Nutr 2001; 131;3208-3211] (measurement of plasma levels of hydroperoxides), erythrocytic GSH according to [Reid M., Badaloo A., Forrester T, Jahoor F. In Vivo rates of erythrocyte glutathione synthesis in adults with sickle cell disease. Am J Physiol Endocrinol Metab. 2006; 291:E73-E79], homocysteine according to [Bleie Ø, Refsum H, Ueland P M et al. Changes in basal and postmethionine load concentration of total homocysteine and cystationine after B vitamin intervention. Am J Clin Nutr 2004; 80:641-648] and morphological evaluation of RBCs by microscopy as described by [Mohanty J G, Eckley D M, J D Williamson et al. Do red blood cell-amyloid interaction alter oxygen delivery in Alzheimer's disease? Adv Exp Med Biol 2008; 614:29-35.]

The compositions of formulations (a) (b) (c) and (d) are given in the following table, under (A) (B) (C) and (D).

TABLE 6

Contents of the four different formulations and relative RDA (recommended daily allowance)

| Formulation A | RDA | Formulation B | RDA | Formulation C | RDA | Formulation D | RDA |
|---|---|---|---|---|---|---|---|
| Vit $B_1$ 1.4 mg | 100 | Carnosine 100 mg | — | Vit E 20 mg (racemic)* | 200 | Vit $B_6$ 1.7 mg | 100 |
| Vit $B_2$ 1.6 mg | 100 | Ginkgo biloba 25 mg | — | Vit C 30 mg | 50 | Vit $B_9$ 0.2 mg | 100 |
| Vit $B_3$ 16 mg | 100 | Coenzyme Q10 10 mg | — | Se 27.5 mcg | 50 | Vit $B_{12}$ 2 mcg | 100 |
| Vit $B_6$ 1.7 mg | 100 | | | L-cysteine 10 mg | | | |
| Vit $B_9$ 0.2 mg | 100 | | | | | | |
| Vit $B_{12}$ 2 mcg | 100 | | | | | | |

The results obtained from determination of d-ROMs test, erythrocytic GSH, homocysteine and fusiform RBCs, before and after a 15-day treatment period with the four antioxidant combinations, are given in Table 7.

TABLE 7

Values for d-ROMs test, erythrocytic GSH and percentage of fusiform RBCs before and after treatment with formulations A, B, C and D (mean values ± SD) in groups of 8 subjects in each

| Variables and times | A | B | C | D |
|---|---|---|---|---|
| d-ROMS [U.CARR] | | | | |
| Basal | 363 ± 42.1 | 385 ± 30.9 | 379 ± 22.7 | 361 ± 35.1 |
| 15 days | 370 ± 33.6 | 383 ± 33.1 | 357 ± 35.8 | 361 ± 29.3 |
| Erythrocytic GSH [mmol/L] | | | | |
| Basal | 1.6 ± 0.53 | 1.5 ± 0.42 | 1.7 ± 0.37 | 1.7 ± 0.37 |
| 15 days | 1.8 ± 0.52$^a$ | 1.6 ± 0.38 | 1.6 ± 0.33 | 1.7 ± 0.47 |
| Homocysteine [mol/L] | | | | |
| Basal | 18.6 ± 1.77 | 19.1 ± 3.02 | 17.4 ± 2.97 | 17.3 ± 2.82 |
| 15 days | 16.8 ± 1.83$^a$ | 18.5 ± 1.83 | 17.1 ± 2.34 | 17.1 ± 2.22 |

TABLE 7-continued

Values for d-ROMs test, erythrocytic GSH and percentage of fusiform RBCs before and after treatment with formulations A, B, C and D (mean values ± SD) in groups of 8 subjects in each

| Variables and times | A | B | C | D |
|---|---|---|---|---|
| Fusiform RBCs [%] | | | | |
| Basal | 14.5 ± 2.07 | 12.3 ± 2.55 | 15.1 ± 2.90 | 15.4 ± 1.92 |
| 15 days | 14.0 ± 2.07 | 12.9 ± 2.42 | 14.6 ± 2.26 | 14.9 ± 2.59 |

$^a$= t-test for interdependent data p < 0.05.

These data show that formulation A produced a slight but significant increase in erythrocytic GSH and a reduction in homocysteine; formulation C produced a slight but significant reduction in OS; in no case were changes in the number of fusiform RBCs noted.

The subsequent third test phase (after a 15-day washout period) conducted with the formulation resulting from combining formulations A+B+C, gave the results shown in table 8 below.

TABLE 8

Values for d-ROMs test, erythrocytic GSH, homocysteine and fusiform RBCs before and after treatment with the combined products contained in formulations A, B, C (mean values ± SD) in groups of 32 subjects in each.

| Variables and times | Formulation A + B + C |
|---|---|
| d-ROMS [U.CARR.] | |
| Basal | 386 ± 23.2 |
| 15 days | 313 ± 18.0$^a$ |
| Erythrocytic GSH [mmol/L] | |
| Basal | 1.6 ± 0.39 |
| 15 days | 2.1 ± 0.47$^a$ |
| Homocysteine | |
| Basal | 18.2 ± 2.51 |
| 15 days | 16.3 ± 2.22$^a$ |
| Fusiform RBCs [%] | |
| Basal | 14.0 ± 2.11 |
| 15 days | 9.4 ± 1.87$^a$ |

$^a$= t-test for interdependent data P > 0.05

These data show that the treatment with the composition derived from combining all the antioxidants in groups (a) (b) and (c) resulted in significant differences in all the parameters.

Surprisingly, it also significantly reduced the presence of fusiform RBCs.

This result was absolutely unexpected, considering that there was no response of any kind with the single groups of antioxidants that act on OS.

Neither in the known art, are there any indications of antioxidants able to contribute a significant improvement in the condition of RBCs.

The results obtained unequivocally show that to protect the functionality of RBCs to in individuals suffering from AD, it is not sufficient to reinforce RBCs' own antioxidant defences but cerebral OS must be reduced with specific antioxidants to avoid that cerebral tissue transfers it by propagation to the RBCs.

The completely new concept forming the basis of the present invention is that it is necessary to reinforce RBCs against their own OS and to simultaneously reduce the amount of OS deriving from their contact with oxidized cerebral tissue.

The new compositions of cerebral antioxidants of the present invention have achieved this object and constitute a crucial step towards the prevention and treatment of Alzheimer's disease.

BIBLIOGRAPHY

1) Hawkins B T, Davis T. The blood-brain barrier/neurovascular unit in health and disease. Pharmacol Rev 2005; 57:173-185.
2) Wang J, Xiong S, Xie C et al. Increased oxidative damage in nuclear and mitochondrial DNA in Alzheimer's disease. J Neurochem 2005; 93:953-962
3) Ding Q, Dimayuga E, Keller J N. Oxidative damage, protein synthesis, and protein degradation in Alzheimer's disease. Curr Alzh Res 2007; 4:73-79
4) Lin M T, Beal M F. Mitochondrial dysfunction and oxidative stress in neurodegenerative diseases. Nature 2006; 433:787-795.
5) Lovell M A, Markesbery W R. Oxidative DNA damage in mild cognitive impairment and late-stage Alzheimer's disease. Nucleic Acids Res 2007; 35:7497-7504.
6) Zhu X, Smith M A, Honda K et al. Vascular oxidative stress in Alzheimers disease. J Neurol Sci 2007; 257:240-246.
7) Dröge W, Schipper M H. Oxidative stress and aberrant signaling in aging and cognitive decline. Aging Cell 2007; 6:361-370.
8) Christen Y. Oxidative stress and Alzheimer disease. Am J Clin Nutr 2000; 71 (suppl):621S-629S.
9) Hachinski V, Munoz D G. Cerebrovascular pathology in ALZHEIMER'S DISEASE: cause, effect or epiphenomenon? Ann N Y Acad Sci 1997; 826:1-6.
10) Smith M A, Vasak K, Knipp M et al. Dimethylarginiase, a nitric oxide regulatory protein, in Alzheimer's disease. Free Radc Biol Med 1998; 25:898-902.
11) Luth H J, Munch G, Gartner U et al. Expression of endothelial and inducible NOS-isoforms is increased in Alzheimer's disease, in APP23 transgenic mice and after experimental brain lesions in rats: evidence for an induction by amyloid pathology. Brain Res 2001; 913:57-67.
12) Heneka M T, Wiesinger H, Dumitrescu-Ozimek L et al. Neuronal and glial coexpression of arginosuccinate synthetase and inducible nitric oxide synthase in Alzheimer disease. J Neuropathol Exp Neurol 2001; 60:906-916.
13) Lee S C, Zhao M L, Hirano A, Dickson D W. Inducible nitric oxide synthase immunoreactivity in the Alzheimer disease hippocampus: association with Hirano bodies, neurofibrillary tangles, and senile plaques. J Neuropathol Exp Neurol 1999-58:1163-1169.

14) Soneja A, Drews M, Malinski T. Role of nitric oxide, nitroxidative and oxidative stress in wound healing. Pharmac Report 2005; 57:108-119.
15) Malinski T. Nitric oxide and nitroxidative stress in ALZHEIMER'S DISEASE. J Alzheimers Dis 2007; 11:207-218.
16) Tagliavini F, Ghiso J, Timmers W F et al. Coexistence of Alzheimer's amyloid precursor protein and amyloid protein in cerebral vessel walls. Lab Invest 1990; 62; 761-767.
17) Mohanty J G, Eckley D M, J D Williamson et al. Do red blood cell-amyloid interaction alter oxygen delivery in Alzheimer's disease? Adv Exp Med Biol 2008; 614:29-35.
18) Singer S J, Dewji N N. Evidence that Perutz's double-stranded subunit structure for -amyloid also applies to their channel-forming structures in membranes. PNAS 2006; 103:1546-1550.
19) Engström I, Ronquist G, Petterson L, Waldenström A. Alzheimer amyloid beta-peptides exhibit ionophore-like properties in human erithrocytes. Eur J Clin Invest 1995; 25:471-476.
20) Ravi L B, Mohanty J G Chrest F J et al. Influence of beta-amyloid fibrils on the interactions between red blood cells and endothelial cells. Neurol Res 2004; 26:579-585.
21) Alhamdani M S S. Impairment of glutathione biosynthetic pathway in uremia and dialysis. Nephrol Dial Transplant. 2005; 20:124-128.
22) Reid M, Badaloo A, Forrester T, Jahoor F. In vivo rates of erythrocytes glutathione synthesis in adults with sickle cell disease. Am J Physiol Endocrinol Metab. 2006; 291:E73-E79.
23) Andreyev A Y, Kushnareva Y E, Starkov A A. Mitochondrial metabolism of reactive species. Biochemistry (Moscow) 2005; 70:200-214
24) Sas K, Robotka H, Toldi J, Vécsei L. Mitochondria, metabolic disturbances, oxidative stress and kynurenine system, with focus on neurodegenerative disorders. J Neurol Sci 2007; 257:221-239.
25) Marlatt M, Lee H, Perry G et al. Sources and mechanism of cytoplasmatic oxidative damage in Alzheimer's disease. Acta Neurobiol Exp. 2004; 64:81-87.
26) Hirai K, Aliev G, Nunomura A et al. Mitochondrial abnormalities in Alzheimers disease. J Neurosci 2001; 21:3017-3023.
27) Mecocci P, Polidori M C, Cherubini A et al. Lymphocyte oxidative DNA damage and plasma antioxidants in Alzheimer disease. Arch Neurol 2002; 59:794-798.
28) Stewart P A, Hayakawa K, Akers M A, Vinters H V. A morphometric study of the blood-brain barrier in Alzheimer's disease Lab Invest 1992; 67:734-742.
29) Blass J P, Gibson G E. The role of oxidative abnormalities in the pathophysiology of Alzheimer's disease. Rev Neurol (paris) 1991; 147:513-525.
30) Metcalfe D D, Thompson H L, Klebanoff S J, Henderson W R. Oxidative degradation of rat mast-cell proteoglycan. Biochem J 1990; 272:51-57.
31) Roberts C R, Roughley P J, Mort J S. Degradation of human proteoglycan aggregates induced by hydrogen peroxide. Biochem J 1989; 259:805-811.
32) Guiotto A, Calderan A, Ruzza P, Bonin G. Carnosine and carnosine-related antioxidants: a review. Curr Med Chem 2005; 12:2293-2315.
33) Hipkiss A R, Brownson C, Carrier M J. Carnosine, the anti-ageing, anti-oxidant dipeptide, may react with protein carbonyl groups. Mech Ageing Dev 2001; 122:1431-1445.
34) Brownson C Hipkiss A R. Could carnosine or related structures suppress Alzheimer's disease? J Alzheimers Dis 2007; 11:229-24

35) Koltermann A, Harkorn A, Koch E et al. *Ginkgo biloba* extract Egb 761 increases endothelial nitric oxide production in vitro and vivo. Cell Mol Life Sci 2007; 64:1715-1722.
36) Napryeyenko O, Borzenko I, GINDEM-NP Study group. *Ginkgo biloba* special extract in dementia with neuropsychiatric features. A randomized placebo-controlled double-blind clinical trial. Arzneimittelforshung 2007; 57:4-11.
37) Mazza M, Capuano A, Bria P, Mazza S. *Ginkgo biloba* and donepezil: a comparison in the treatment of Alzheimer's dementia in a randomized placebo-controlled double-blind study. Eur J Neurol 2006; 13:981-985.
38) Seshadri S, Beiser A, Selhub J et al. Plasma homocysteine as risk factor for dementia and Alzheimer's disease. NEJM 2002; 346:476-483.
39) Ravaglia G, Forti P, Maioli F et al. Homocysteine and folate as risk factors for dementia and Alzheimer disease. Am J Clin Nutr 2005; 82:636-643.
40) Babiloni, C, Bosco P, Ghidoni R et al. Homocysteine and electroencephalographic rhythms in Alzheimer's disease. Neuroscience 2007; 145, 942-954.
41) Pogribna M, Melnik 5, Pogribni I, Chango et al. Homocysteine metabolism with Down Syndrome: in vitro stimulation. Am J Human Genet 2001; 69:88-95.
42) Selkoe D J. Normal and abnormal biology of the β-amyloid precursor protein. Annu Rev Neurosci 1994; 17:489-517.
43) Näslund J, Haroutonian V, Mohs R et el. Correlation between elevated levels of amyloid β-peptide in the brain and cognitive decline. JAMA 2000; 283:1571-1577.
44) Kontush A. Amyloid-beta: an antioxidant that becomes a pro-oxidant and critically contributes to Alzheimer's disease. Free Rad Biol Med 2001; 31:1120-1131.
45) Butterfield D A. Amyloid beta-peptide (1-42)-induced oxidative stress and neurotoxicity: implication for neurodegeneration in Alzheimer's disease brain. A review. Free Rad Res 2002; 36:1307-1313.
46) Suo Z, Su G, Kundtz A et al. A beta vasoactivity in vivo. Ann N Y Acad Sci 2000; 903:156-163.
47) Cleary J P, Walsh D M, Hofmeister J J et al. Natural oligomers of the amyloid-beta protein specifically disrupt cognitive function. Nat Neurosci 2005; 8:79-84.
48) Walsh D M, Selkoe D J. Oligomers on the brain: the emerging role of soluble protein aggregates in neurodegeneration. Protein Pept Lett 2004; 11:213-228.
49) Bleie Ø, Refsum H, Ueland P M et al. Changes in basal and postmethionine load concentration of total homocysteine and cystathionine after B vitamin intervention. Am J Clin Nutr 2004; 80:641-648.
50) Lee B J, Huang M C, Chung L J et al. Folic acid and vitamin B12 are more effective than vitamin B6 in lowering fasting plasma homocysteine concentration in patients with coronary artery disease. Eur J Clin Nutr 2004; 58:481-487.
51) NcKinley M C, McNulty H, McPartlin J et al. Low-dose vitamin B6 effectively lowers fasting homocysteine in healthy elderly person who are folate and riboflavin replete. Am J Clin Nutr 2001; 73:759-764.
52) Bønaa K H, Njølstad N J, Ueland P M et al. Homocysteine lowering and cardiovascular events after acute myocardial infarction. NEJM 2006; 354:1578-1588.
53) Ebbing M, Bleie Ø, Ueland P M et al. Mortality cardiovascular events in patients treated with homocysteine-lowering B vitamin after coronary.
54) Jatoi A, Kahanic S P, Frytak S et al. Donepezil and Vitamin E for preventing cognitive dysfunction in small cell lung cancer patients: preliminary results and suggestions for future study design. Support Care cancer. 2005; 13:66-69.

The invention claimed is:

1. A pharmaceutical composition comprising, as the only active ingredients, 40 to 50 wt % of carnosine, 0.5 to 1 wt % of thiamine, 0.5 to 1 wt % of riboflavin, 5 to 12 wt % of nicotinamide, 0.6 to 1.4 wt % of pyridoxine, 10 to 20 wt % of vitamin C, 5 to 12 wt % of vitamin E, 1 to 7 wt % of coenzyme $Q_{10}$, 0.5 to 5 wt % of β-carotene, 1 to 7 wt % of L-cysteine, 8 to 15 wt % of Ginkgo biloba extract.

2. A medicament for stabilizing and treating Alzheimer's disease and cognitive dysfunctions connected thereto comprising the pharmaceutical composition according to claim 1.

3. The pharmaceutical composition according to claim 1, comprising 42 to 45 wt % of carnosine, 0.6 to 0.8 wt % of thiamine, 0.6 to 0.8 wt % of riboflavin, 6 to 10 wt % of nicotinamide, 0.8 to 1.2 wt % of pyridoxine, 12 to 15 wt % of vitamin C, 7 to 10 wt % of vitamin E, 3 to 6 wt % of coenzyme $Q_{10}$, 1.5 to 3 wt % of β-carotene, 3 to 6 wt % of L-cysteine, 10 to 13 wt % of Ginkgo biloba extract.

4. A pharmaceutical composition consisting of 44.5 to 45 wt % of carnosine, 0.6 to 0.7 wt % of thiamine, 0.65 to 0.75 wt % of riboflavin, 7.5 to 9 wt % of nicotinamide, 0.8 to 1 wt % of pyridoxine, 0.07 to 0.1 wt % of folic acid, 0.0004 to 0.0007 wt % of cyanocobalamin, 13 to 14 wt % of vitamin C, 8.5 to 9.5 wt % of vitamin E, 4 to 5 wt % of coenzyme $Q_{10}$, 2 to 2.5 wt % of β-carotene, 0.01 to 0.02 wt % of selenium, 4 to 5 wt % of L-cysteine, and 11 to 12 wt % of Ginkgo biloba extract.

5. The pharmaceutical composition according to claim 4, consisting of carnosine 100 mg, thiamine 1.4 mg, riboflavin 1.6 mg, nicotinamide 18 mg, pyridoxine 2 mg, folic acid 200 µg, cyanocobalamin 1 µg, vitamin C 30 mg, vitamin E 20 mg, coenzyme Q10 10 mg, β-carotene 800 Retinol Equivalents, selenium 27.5 µg, L-cysteine 10 mg and Ginkgo biloba extract 25 mg.

6. A method for stabilizing and treating Alzheimer's disease and cognitive dysfunctions connected thereto, comprising the step of administering an effective amount of the pharmaceutical composition according to claim 1 to a patient in need thereof.

7. The method according to claim 6, wherein each active ingredient is administered in an amount equal to or less than the RDA (Recommended Daily Allowance).

8. The method according to claim 6, wherein a unitary dose of the pharmaceutical composition comprises 90 to 110 mg of carnosine, 1.2 to 1.7 mg of thiamine, 1.4 to 1.8 mg of riboflavin, 14 to 24 mg of nicotinamide, 1 to 3 mg of pyridoxine, 25 to 42 mg of vitamin C, 12 to 25 mg of vitamin E, 5 to 15 mg of coenzyme $Q_{10}$, 2 to 9 mg of β-carotene, 5 to 15 mg of L-cysteine, 20 to 32 mg of Ginkgo biloba extract.

9. The method according to claim 8, wherein said unitary dose of the pharmaceutical composition is daily administered in an amount of 30 to 300% depending on the seriousness of the disease to be treated.

10. The method according to claim 6, wherein said unitary dose of the pharmaceutical composition consists of carnosine 100 mg, thiamine 1.4 mg, riboflavin 1.6 mg, nicotinamide 18 mg, pyridoxine 2 mg, folic acid 200 µg, cyanocobalamin 1 µg, vitamin C 30 mg, vitamin E 20 mg, coenzyme Q10 10 mg, β-carotene 800 Retinol Equivalents, selenium 27.5 µg, L-cysteine 10 mg and Ginkgo biloba extract 25 mg.

11. The method according to claim 10, wherein said unitary dose of the pharmaceutical composition is daily administered in an amount of 30 to 300% depending on the seriousness of the disease to be treated.

* * * * *